United States Patent
Chen et al.

(10) Patent No.: US 10,960,006 B2
(45) Date of Patent: Mar. 30, 2021

(54) TOPICAL FORMULATIONS COMPRISING TOFACITINIB

(71) Applicant: TWi Pharmaceuticals, Inc., Taipei (TW)

(72) Inventors: Chih-Ming Chen, Taipei (TW); Guang-Wei Lu, Irvine, CA (US); Ling-Ying Liaw, Taipei (TW); Fan-Lun Liu, Taipei (TW); Shih-Fen Liao, Taipei (TW); Chou-Hsiung Chen, Taipei (TW); Yu-Han Kao, Taipei (TW); Yu-Yin Chen, Taipei (TW)

(73) Assignee: TWi Pharmaceuticals, Inc., Taipei (TW)

( * ) Notice: Subject to any disclaimer, the term of this patent is extended or adjusted under 35 U.S.C. 154(b) by 0 days.

(21) Appl. No.: 16/254,076

(22) Filed: Jan. 22, 2019

(65) Prior Publication Data

US 2019/0231782 A1    Aug. 1, 2019

Related U.S. Application Data

(60) Provisional application No. 62/624,567, filed on Jan. 31, 2018.

(51) Int. Cl.
| | |
|---|---|
| *A61K 31/519* | (2006.01) |
| *A61K 9/00* | (2006.01) |
| *A61K 9/06* | (2006.01) |
| *A61P 37/02* | (2006.01) |
| *A61K 47/20* | (2006.01) |
| *A61K 47/38* | (2006.01) |
| *A61K 47/10* | (2017.01) |

(52) U.S. Cl.
CPC .......... *A61K 31/519* (2013.01); *A61K 9/0014* (2013.01); *A61K 9/06* (2013.01); *A61K 47/10* (2013.01); *A61K 47/20* (2013.01); *A61K 47/38* (2013.01); *A61P 37/02* (2018.01)

(58) Field of Classification Search
CPC ........................... C07D 487/04; A61K 31/519
See application file for complete search history.

(56) References Cited

U.S. PATENT DOCUMENTS

| | | | | |
|---|---|---|---|---|
| 9,409,909 B2 * | 8/2016 | Charvat | ............... | C07D 209/08 |
| 9,763,866 B2 * | 9/2017 | Christiano | ........... | A61K 31/519 |
| 10,092,541 B2 * | 10/2018 | Day | ................... | A61K 39/3955 |
| 2012/0258976 A1 | 10/2012 | Murphy et al. | | |
| 2013/0178440 A1 * | 7/2013 | Seykora | ............. | A61K 31/4745 |
| | | | | 514/47 |
| 2015/0335644 A1 | 11/2015 | Seykora | | |
| 2016/0185822 A1 * | 6/2016 | Ponsati Obiols | .... | C07K 14/575 |
| | | | | 424/450 |
| 2016/0235812 A1 * | 8/2016 | Bruhn | ................ | A61K 38/1716 |
| 2017/0174772 A1 * | 6/2017 | Nirula | ................ | C07K 16/2866 |

FOREIGN PATENT DOCUMENTS

| | | | | |
|---|---|---|---|---|
| WO | WO-02096909 A1 * | 12/2002 | ........... | C07D 211/56 |
| WO | 2012/135338 A1 | 10/2012 | | |
| WO | WO-2012137111 A1 * | 10/2012 | ........... | A61K 9/0014 |
| WO | WO-2014013014 A1 * | 1/2014 | | |

OTHER PUBLICATIONS

P. Sjoevall et al., 86 Analytical Chemistry (2014) (Year: 2014).*
T. Torres et al., 76 Drug Development Research, 215-227 (2015) (Year: 2015).*
W.C. Ports et al., 169 British Journal of Dermatology, 137-145 (2013) (Year: 2013).*
T. Sakimoto et al., 145 Experimental Research, 110-117 (2016) (Year: 2016).*
J. Meephansan et al., 309 Arch Dermatol Res, 729-738 (2017) (Year: 2017).*
International Search Report and Written Opinion for corresponding PCT Application No. PCT/US19/14524 dated Apr. 11, 2019.

* cited by examiner

*Primary Examiner* — Paul V Ward
(74) *Attorney, Agent, or Firm* — Wood, Phillips, Katz, Clark & Mortimer

(57) ABSTRACT

A topical formulation comprising (a) a therapeutically effective amount of tofacitinib; (b) at least one solvent; and (c) optionally one or more other pharmaceutically acceptable excipients is provided. Also provided is a method for treating and/or preventing autoimmune diseases in a subject administering said topical formulation.

16 Claims, 6 Drawing Sheets
(2 of 6 Drawing Sheet(s) Filed in Color)

TOPICAL FORMULATIONS COMPRISING TOFACITINIB

BACKGROUND OF THE INVENTION

Field of the Invention

The present invention is directed to topical formulations comprising tofacitinib. The invention is also directed to uses of said topical formulation for the treatment of autoimmune disorders and particularly, for the treatment of vitiligo and atopic dermatitis.

DESCRIPTIONS OF THE RELATED ART

Tofacitinib, 3-((3R,4R)-4-methyl-3-[methyl-(7H-pyrrolo[2,3-d]pyrimidin-4-yl)-amino]-piperidin-1-yl)-3-oxopropionitrile, has the chemical formula $C_{16}H_2ON_6O$ and the following structural formula (I).

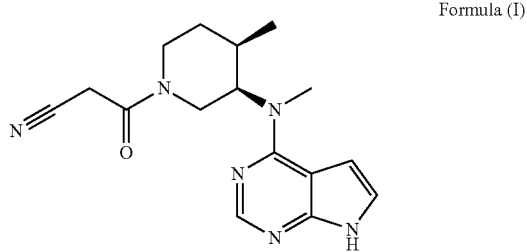 [SMILES: C[C@@H]1CCN(C(=O)CC#N)C[C@@H]1N(C)c1ncnc2[nH]ccc12]

Formula (I)

Tofacitinib is useful as an JAK inhibitor or an immunosuppressive agent for organ transplants, xeno transplantation, lupus, multiple sclerosis, rheumatoid arthritis, psoriasis, psoriatic arthritis, Type I diabetes and complications from diabetes, cancer, asthma, atopic dermatitis, autoimmune thyroid disorders, ulcerative colitis, Crohn's disease, Alzheimer's disease, Leukemia and other indications where immunosuppression would be desirable.

Currently, tofacitinib citrate is approved in the US under the brand name XELJANZ®. XELJANZ® is an immediate release tablet form with 8 mg tofacitinib citrate (equivalent to 5 mg tofacitinib) and being administered twice a day XELJANZ® is also available as a once-daily tablet called XELJANZ® XR XELJANZ® XR is approved in the extended-release tablets form with 17.77 mg tofacitinib citrate (equivalent to 11 mg tofacitinib). Both XELJANZ® and XELJANZ® XR tablets are supplied for oral administration and are indicated for the treatment of rheumatoid arthritis.

Some adverse side effects, such as upper respiratory tract infections, headache, diarrhea, and cold symptoms, have been observed after oral administration of tofacitinib citrate. Topical dosage forms of tofacitinib have been proposed for locally treatment and minimizing these side effects. U.S. Pat. No. 8,541,426 discloses a topical tofacitinib composition for treating dry eye disorders. US Pat. Application Pub. No. 20120258976 discloses a topical ointment formulation comprising tofacitinib free base and oleyl alcohol for use in treatment of psoriasis.

However, the composition in U.S. Pat. No. 8,541,426 is a topical formulation for ophthalmic administration, and thus its efficacy and safety for skin application are unknown. US 20120258976 provides in vitro percutaneous flux data to generate cumulative permeation and flux profiles after administering the topical ointment formulation, but mentions little information about the retention rate of tofacitinib in the skin. Thus, one cannot know whether tofacitinib may provide a prolonged local treatment effect after administration. In addition, these prior art compositions are mainly used for the treatment of ocular disorders or psoriasis, and thus their treatment efficacy on other skin diseases is unclear.

Considering the limitation of the above literature, there is a need in the art for a topical formulation of tofacitinib with a desired retention rate as well as other physicochemical properties and adapted to autoimmune diseases.

SUMMARY OF THE INVENTION

An object of the present invention is to provide a topical formulation comprising (a) a therapeutically effective amount of tofacitinib; (b) at least one solvent; and (c) optionally, one or more other pharmaceutically acceptable excipients.

Another object of the present invention is to provide a topical formulation comprising (a) a therapeutically effective amount of tofacitinib citrate; (b) dimethyl sulfoxide; (c) optionally, propylene glycol; (d) optionally, a thickening agent; (e) optionally, an antioxidant; and (f) optionally, one or more other pharmaceutically acceptable excipients.

Still another object of the present invention is to provide a method for treating and/or preventing autoimmune diseases in a subject, comprising administering the topical formulation of the present invention to said subject.

The detailed technology and preferred embodiments implemented for the subject invention are described in the following paragraphs accompanying the appended drawings for people skilled in this field to well appreciate the features of the claimed invention.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

Definitions

Figure 1:
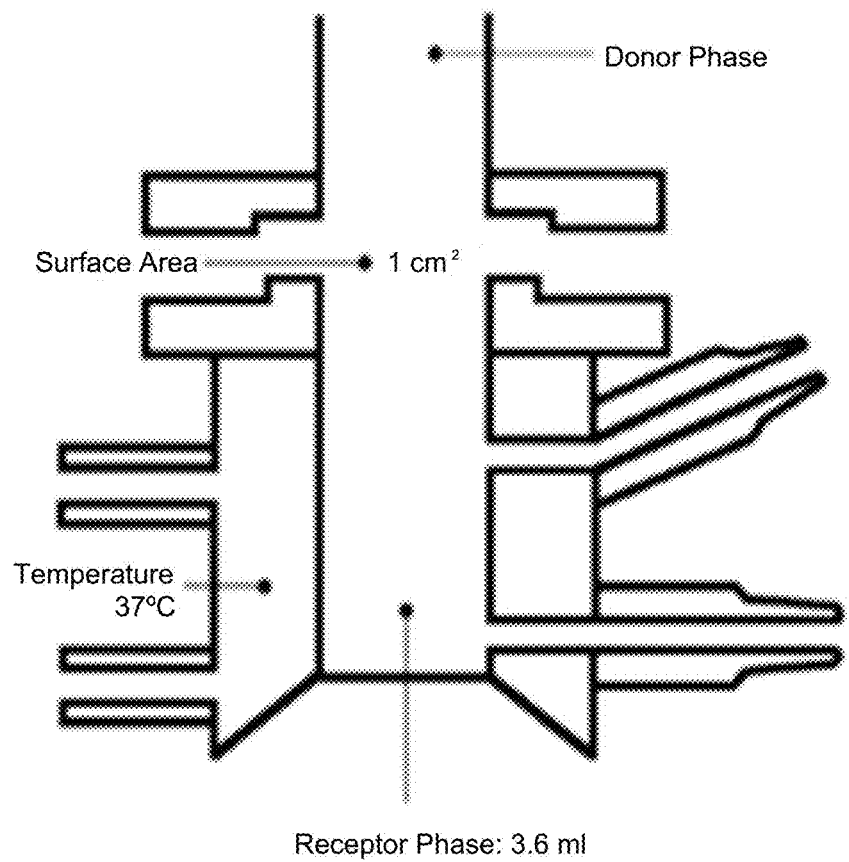
FIG. 1 is a schematic showing a flow-through diffusion cell used in the in-vitro penetration/retention study.

The term "tofacitinib," as used herein, refers to tofacitinib in the form of free base, pharmaceutically acceptable salts, racemates, diastereomers, isomers, analogs, and mixtures thereof.

The term "therapeutically effective amount," as used herein, refers to an amount that alleviates or reduces one or more symptoms of a disease.

The term "degradation product," as used herein, refers to an unwanted chemical or impurity that can develop during the manufacturing, transportation, and storage of drug products and can affect the efficacy of pharmaceutical products. It can form in response to changes in light, temperature, pH, and humidity, or due to inherent characteristics of active ingredients, such as their reaction with excipients or on contact with the packaging.

In addition, unless otherwise stated herein, the terms "a (an)", "the" or the like used in this specification and the claims shall be understood to encompass both the singular form and the plural form.

As described above, the present invention provides a topical formulation with improved physicochemical properties that are beneficial for the treatment of autoimmune diseases.

The topical formulation of the present invention comprises (a) a therapeutically effective amount of tofacitinib; (b) at least one solvent; and (c) optionally, one or more other pharmaceutically acceptable excipients.

In some embodiments, the topical formulation can be formulated to different dosage forms, for example, a solution, a suspension, a cream, an ointment, a lotion and a gel. Preferably, the topical formulation is a solution or a gel. More preferably, the topical formulation is a gel.

In some embodiments, tofacitinib is in the form of a pharmaceutically acceptable salt. Such salts include, but are not limited to, citrate salt, hydrochloride salt, hydrobromide salt, oxalate salt, nitrate salt, sulfate salt, phosphate salt, fumarate salt, succinate salt, maleate salt, besylate salt, tosylate salt, palmitate salt and tartrate salt. Preferably, the pharmaceutically acceptable salt is citrate salt.

In some embodiments, tofacitinib in the formulation is present at a concentration from about 0.1% w/w to about 5% w/w, preferably about 1% w/w to about 4% w/w, based on the total weight of the formulation.

In some embodiments, the solvent can be, for example, dimethyl sulfoxide, propylene glycol, glycerin, poly ethylene glycol, isopropyl alcohol, methanol, sodium pyrrolidone carboxylate, 2-hydroxypropyl-γ-cyclodextrin, acetone, purified water, ethanol, 1-propanol, butanediol, 2-(2-ethoxyethoxy)ethanol (transcutol), or a combination thereof. Preferably, tofacitinib is freely soluble in the solvent. More preferably, the solvent is dimethyl sulfoxide.

In one embodiment, the solvent is a combination of dimethyl sulfoxide with at least one of propylene glycol, ethanol, and water.

In some embodiments, the solvent is present at a concentration from about 40% w/w to about 99.9% w/w, preferably about 70% w/w to about 99% w/w, more preferably about 90% w/w to about 97% w/w, based on the total weight of the formulation.

The topical formulation of the present invention may include one or more other pharmaceutically acceptable excipients. For example, the pharmaceutically acceptable excipients can be selected from a thickening agent, a stabilizer, an antioxidant, a chelating agent, an oily material, an emulsifier, a penetration enhancer, a pH adjusting agent, a preservative, an antimicrobial agent, an opacifier, a fragrance, a colorant, a gelling agent, a moisturizer, a surfactant, etc.

The pharmaceutically acceptable excipients used in the formulation of the present invention can act in more than one way. For example, a thickening agent can also function as a gelling agent, a penetration enhancer, etc., and a solvent can also function as a stabilizer (e.g., suppressing the total degradation products of tofacitinib).

In one embodiment, the topical formulation of the present invention does not include oleyl alcohol.

In some embodiments, the topical formulation comprises a thickening agent. Preferably, the thickening agent can be, for example, cellulose derivative, polyvinylpyrrolidone, carbomer polymer, carbomer derivative, maltodextrin, polydextrose, dextrates, carboxypolymethylene, polyvinyl alcohol, poloxamers, polyethylene glycols, or a combination thereof. More preferably, the thickening agent is hydroxypropyl cellulose.

In some embodiments, the thickening agent is present at a concentration from about 0.05% w/w to about 5% w/w, preferably about 0.1% w/w to about 4% w/w, more preferably about 1% w/w to about 3% w/w, based on the total weight of the formulation.

In some embodiments, the topical formulation comprises a gelling agent. Preferably, the gelling agent can be, for example, cellulose derivative, polyvinylpyrrolidone, carbomer polymer, carbomer derivative, maltodextrin, polydextrose, dextrates, carboxypolymethylene, polyvinyl alcohol, poloxamers, polyethylene glycols, or a combination thereof.

In some embodiments, the gelling agent is present at a concentration from about 0.05% w/w to about 5% w/w, preferably about 0.1% w/w to about 4% w/w, more preferably about 1% w/w to about 3% w/w, based on the total weight of the formulation.

In some embodiments, the topical formulation comprises an antioxidant. Preferably, the antioxidant can be, for example, butylated hydroxyanisole, butylated hydroxytoluene, vitamin C, vitamin E, vitamin A, lutein, lycopene, retinyl palmitate, potassium metabisulfite, sodium metabisulfite, sodium thiosulfate pentahydrate, 3,4-dihydroxybenzoic acid, propyl gallate, alpha-lipoic acid, ascorbyl palmitate, sodium pyrosulfite, ubiquinone, selenium, or a combination thereof. More preferably, the antioxidant is butylated hydroxyanisole.

In some embodiments, the antioxidant is present at a concentration from about 0.05% w/w to about 5% w/w, preferably about 0.1% w/w to about 3% w/w, based on the total weight of the formulation.

In some embodiments, the topical formulation comprises a chelating agent. Preferably, the chelating agent can be, for example, ethylenediaminetetraacetic acid (EDTA), a salt of EDTA, desferrioxamine B, deferoxamine, dithiocarb sodium, penicillamine, pentetate calcium, a sodium salt of pentetic acid, succimer, trientine, nitrilotriacetic acid, trans-diaminocyclohexanetetraacetic acid (DCTA), diethylenetriaminepentaacetic acid, bis(aminoetliyl) glycolether-N,N,N', N'-tetraacetic acid, iminodiacetic acid, citric acid, tartaric acid, fumaric acid, or a combination thereof. More preferably, the chelating agent is ethylenediaminetetraacetic acid (EDTA).

In some embodiments, the chelating agent is present at a concentration from about 0.005% w/w to about 0.5% w/w, preferably about 0.01% w/w to about 0.1% w/w, based on the total weight of the formulation.

In some embodiments, the topical formulation comprises a preservative. Preferably, the preservative can be, for example, methylparaben, propylparaben, benzyl alcohol, benzoic acid, phenol, or a combination thereof. More preferably, the preservative is methylparaben.

In some embodiments, the preservative is present at a concentration from about 0.005% w/w to about 2% w/w, preferably about 0.05% w/w to about 0.5% w/w, based on the total weight of the formulation.

In order to treat skin-related autoimmune disorders, it is desired to develop a topical formulation that provides a balance of tofacitinib penetration and retention in the skin. The therapeutic agent penetrates through the stratum corneum easily to reach the target site (e.g., dermis or epidermis, where skin disorders may occur) and is retained in the target skin layer to produce locally therapeutic effects. The topical formulation of the present invention achieves optimal balance of penetration and retention and demonstrates high retention rate in skin.

In some embodiments, when the topical formulation of the present invention is applied to the skin of a subject, the amount of tofacitinib retained in the skin is more than that penetrating through the skin into the blood or systemic circulation, for 4 hours, preferably 8 hours, and most preferably 12 hours after the application.

In one embodiment, when the topical formulation is applied to the skin of a subject, the amount of tofacitinib retained in the skin is at least about 4.7 times, preferably at least about 5 times, more preferably at least about 10 times, and most preferably at least about 100 times more than that penetrating through the skin into the blood or systemic circulation, for 8 hours after the application.

The topical formulation of the present invention may undergo degradation to form degradation products due to its inherent characteristics or changes in light, temperature, pH, or humidity during the manufacturing, transportation, and storage. Even a small amount of degradation products can affect pharmaceutical safety because of the potential to cause adverse effects in patients. Therefore, it is necessary to prevent the formation of degradation products and extend the shelf life of tofacitinib products.

The topical formulation of the present invention can stabilize tofacitinib and prevent forming degradation in the formulation.

In a preferred embodiment, the total degradation products of the tofacitinib formulation are less than 2% of tofacitinib present initially after the formulation is stored at room temperature (i.e., from 20° C. to 27° C.) for at least 1 month, preferably at least 3 months, preferably at least 4 months, preferably at least 5 months, preferably at least 6 months, and more preferably at least 8 months.

In one embodiment, the topical formulation of the present invention comprises (a) a therapeutically effective amount of tofacitinib citrate; (b) dimethyl sulfoxide; (c) optionally propylene glycol; (d) optionally, a thickening agent; (e) optionally, an antioxidant; and (f) optionally, one or more other pharmaceutically acceptable excipients. In some embodiments, the topical formulation comprises (a) about 0.1% w/w to about 5% w/w of tofacitinib citrate; (b)

about 1% w/w to about 80% w/w of dimethyl sulfoxide; (c) optionally, about 10% w/w to about 60% w/w of propylene glycol; (d) optionally, about 0.05% w/w to about 5% w/w of hydroxypropyl cellulose; (e) optionally, about 0.05% w/w to about 5% w/w of butylated hydroxyanisole; and (f) optionally, one or more other pharmaceutically acceptable excipients, based on the total weight of the topical formulation.

In one embodiment, the topical formulation is a cream formulation. A cream is easy to spread on the skin's surface (i.e., easy to apply), less greasy compared to an ointment, easily water washable, easy to wipe away, suitable for sensitive, dry skin and also suitable for acute lesions.

Creams are semi-solid emulsions of oily phase and water phase. They are divided into two types: oil-in-water (O/W) form which is composed of small droplets of oil dispersed in a continuous water phase, and water-in-oil (W/O) form which is composed of small droplets of water dispersed in a continuous oily phase. Oil-in-water creams are more comfortable and cosmetically acceptable as they are less greasy and more easily washed off using water. Water-in-oil creams are more difficult to handle but many drugs which are incorporated into creams are hydrophobic and will be released more readily from a water-in-oil cream than an oil-in-water cream. Water-in-oil creams are also more moisturizing as they provide an oily barrier which reduces water loss from the stratum corneum, the outermost layer of the skin. Emulsifiers are used in creams to mix water with oils. Since water and oil do not mix but stay separated, an emulsifier is necessary to form a homogenous mixture keeping water and oil together.

In one embodiment, the topical cream formulation of the present invention comprises (a) a therapeutically effective amount of tofacitinib; (b) at least one solvent; (c) an oily material; (d) an emulsifier; and (e) optionally, one or more other pharmaceutically acceptable excipients. Preferably, said solvent is a combination of dimethyl sulfoxide and water (i.e., an aqueous DMSO solution).

In some embodiments, tofacitinib in the topical cream formulation is present at a concentration from about 0.1% w/w to about 5% w/w, preferably about 1% w/w to about 4% w/w, based on the total weight of the formulation.

In some embodiments, the solvent in the topical cream formulation is present at a concentration from about 40% w/w to about 99% w/w, preferably about 60% w/w to about 95% w/w, more preferably about 75% w/w to about 90% w/w, based on the total weight of the formulation.

In some embodiments, the topical cream formulation comprises an oily material. Preferably, the oily material can be, for example, vegetable oil, mineral oil, petrolatum, medium chain triglyceride (MCT) oil, soybean oil, sesame-seed oil, peanut oil, sunflower oil, cotton-seed oil, castor oil, olive oil, animal oils, fatty acids, synthetic oils, natural and synthetic glycerides, sterol esters, fatty alcohols, silicone oil, or a combination thereof. More preferably, the oily material is mineral oil, medium chain triglyceride (MCT) oil, or castor oil. Most preferably, the oily material is castor oil.

In some embodiments, the oily material is present at a concentration from about 0.05% w/w to about 60% w/w, preferably about 1% w/w to about 55% w/w, more preferably about 10% w/w to about 50% w/w, based on the total weight of the formulation.

In some embodiments, the topical cream formulation comprises an emulsifier. Preferably, the emulsifier can be, for example, cetearyl alcohol, sorbitan isostearate, glyceryl stearate, PEG-100 stearate, potassium olivate, polysorbate, sorbitan ester, decyl glucoside, hydroxyethyl acrylate/sodium acryloyldimethyl taurate copolymer, or a combination thereof. More preferably, the emulsifier is hydroxyethyl acrylate/sodium acryloyldimethyl taurate copolymer.

In some embodiments, the emulsifier is present at a concentration from about 0.05% w/w to about 20% w/w, preferably about 1% w/w to about 15% w/w, based on the total weight of the formulation.

In some embodiments, the topical cream formulation of the present invention comprises (a) about 0.1% w/w to about 5% w/w of tofacitinib; (b) about 40% w/w to about 99% w/w of a solvent; (c) about 0.05% w/w to about 60% w/w of an oily material; (d) about 0.05% w/w to about 20% w/w of an emulsifier; and (e) optionally one or more other pharmaceutically acceptable excipients. Preferably, said solvent is a combination of dimethyl sulfoxide and water.

In some embodiments, the topical cream formulation of the present invention comprises (a) about 1% w/w to about 4% w/w of tofacitinib; (b) about 60% w/w to about 95% w/w of a solvent; (c) about 1% w/w to about 55% w/w of an oily material; (d) about 1% w/w to about 15% w/w of an emulsifier; and (e) optionally one or more other pharmaceutically acceptable excipients. Preferably, said solvent is a combination of dimethyl sulfoxide and water.

Considering that the topical formulation of the present invention has excellent retention rate and stability of tofacitinib, it may provide more effective treatment for skin related autoimmune diseases. Furthermore, it may also be an alternative to oral therapy for non-skin related autoimmune disease.

Thus, the topical formulation of the present invention can be used in treatment and/or prevention of autoimmune diseases including vitiligo, atopic dermatitis, psoriasis, epidermolysis bullosa acquista, pemphigus vulgaris, IgA-mediated bullous dermatoses, systemic lupus erythematosus, alopecia areata, porphyria, scleroderma, multiple sclerosis, rheumatoid arthritis and skin complication of Type I diabetes.

Vitiligo is a condition that causes skin depigmentation due to loss of function and/or death of melanocytes in the epidermis, producing milky-white patches on affected skin. The lightened lesions of the skin generally have greater susceptibility to the damaging effects of the sun, premature aging and possibly skin cancer. Treatment options for vitiligo include medical treatments, surgical therapies, phototherapy and adjunctive treatments. Topical corticosteroid therapy has a reported success rate of up to 56%; however, long-term use of corticosteroids can result in thinning of the skin, stretch marks, and dilation of blood vessels.

In one embodiment, the topical formulation of the present invention is used in the treatment and/or prevention of vitiligo, as an alternative to topical corticosteroid therapy.

Atopic dermatitis (AD) is caused by a defect of a stratum corneum, a protective wall located in the outermost part of the skin. AD is a chronic/relapsing inflammatory skin disease characterized by intense pruritus (e.g., severe itch) and by scaly and dry eczematous lesions. Steroid agents can act as an anti-inflammatory agent and immuno-suppressant and have positive effect in treating atopic dermatitis, but if used over a long period of time, side effects such as skin-weakening, symptom of systemic hormone, and toxicity can occur.

In one embodiment, the topical formulation of the present invention is used in the treatment and/or prevention of atopic dermatitis, as an alternative to steroid therapy.

In some embodiments, the topical formulation is a once or twice-daily formulation. That is, the formulation is applied to the skin of a subject once a day or twice a day.

In some embodiments, tofacitinib is the sole active ingredient in the formulation. These embodiments may include ingredients that could be used as active ingredients in prior art formulations, as long as the amounts of these ingredients in the provided formulations are at sub-therapeutic levels for the purposes of the provided formulations in the instant application. The invention also provides embodiments wherein tofacitinib is not the only active ingredient and can be combined with other active ingredients.

In some embodiments, tofacitinib is administered to the skin at a daily therapeutically effective dose of about 0.5 mg/cm$^2$ to about 60 mg/cm$^2$.

The present invention also provides a method for treating and/or preventing autoimmune diseases in a subject, comprising administering the topical formulation of the present invention to the subject.

Preferably, the autoimmune disease is vitiligo or atopic dermatitis.

Hereinafter, the present invention will be further illustrated with reference to the following examples. However, these examples are only provided for illustrative purposes, but not to limit the scope of the present invention in any way.

Example 1

Solubility of Tofacitinib Citrate

A solubility study was conducted in the course of formulation development. Excess of tofacitinib citrate was added to various solvent listed in Table 1. The suspension was stirred overnight and filtered through 0.22 μm filter. The filtrate was diluted into suitable concentration. The concentration of tofacitinib citrate in each solvent was determined by HPLC method. The solubility results of tofacitinib citrate in various solvents are summarized in Table 1.

TABLE 1

Solubility of Tofacitinib Citrate

| API | Solvent | Solubility (mg/mL) | Descriptive Term |
|---|---|---|---|
| Tofacitinib Citrate | Dimethyl sulfoxide (DMSO) | >100 | Freely soluble |
| | Ethanol | 0.48 | Very slightly soluble |
| | Propylene Glycol (PG) | 1.92 | Slightly soluble |
| | H$_2$O | 3.00 | Slightly soluble |
| | 0.1N HCl | 23.86 | Sparingly soluble |
| | pH 3.0, 50 mM Citrate Buffer | 0.60 | Very slightly soluble |
| | pH 4.5, 50 mM Acetate Buffer | 1.81 | Slightly soluble |
| | pH 4.5, 50 mM Acetate Buffer/PEG300 = 70/30 | 3.16 | Slightly soluble |
| | pH 7.5, 50 mM Phosphate Buffer | 0.12 | Very slightly soluble |
| | pH 7.5, 50 mM Phosphate Buffer/PEG300 = 70/30 | 1.59 | Slightly soluble |
| | pH 6.8, 50 mM Phosphate Buffer | 0.12 | Very slightly soluble |
| | pH 9.0, 50 mM Phosphate Buffer | 0.12 | Very slightly soluble |

The results showed that tofacitinib citrate is freely soluble in dimethyl sulfoxide (DMSO), slightly soluble in water and propylene glycol (PG), and very slightly soluble in ethanol. To prepare the desired concentration of tofacitinib topical formulation (32 mg/mL), DMSO was chosen as a solvent. It also showed that the solubility of tofacitinib citrate is pH-dependent. The aqueous solubility of tofacitinib citrate decreases as pH increases from 1 to 3, slightly increases at pH 4.5 and remains relatively low above pH 6.8.

Example 2

Compatibility Study of Tofacitinib Citrate

At the early stage of formulation development, to understand the potential incompatibilities between tofacitinib citrate and excipients, several compatibility tests were performed. Specifically, vials with rubber stoppers containing the mixtures of dissolved tofacitinib citrate with excipients, as specified in Table 2 below, were incubated in a chamber under the condition of 60° C. for seven days. The total degradation products in the mixtures were further analyzed by HPLC.

TABLE 2

Compatibility Study of Tofacitinib Citrate

| The Mixtures of Dissolved Tofacitinib Citrate with Excipients 60° C., 1 Week | Total Degradation Products (%) |
|---|---|
| Tofacitinib Citrate | 0.06 |
| Tofacitinib Citrate/DMSO | 4.17 |
| Tofacitinib Citrate/propylene glycol/DMSO | 0.47 |
| Tofacitinib Citrate/isopropyl alcohol (IPA)/DMSO | 0.51 |
| Tofacitinib Citrate/poly ethylene glycol 400 (PEG400)/DMSO | 5.23 |
| Tofacitinib Citrate/Glycerin/DMSO | 3.67 |
| Tofacitinib Citrate/methanol/DMSO | 2.06 |
| Tofacitinib Citrate/0.5N NaOH/DMSO | 2.19 |
| Tofacitinib Citrate/hydroxypropyl cellulose (HPC)/DMSO | 4.96 |
| Tofacitinib Citrate/ethanol/DMSO | 1.01 |

The compatibility study results are shown in Table 2. Although tofacitinib citrate exhibits good solubility in DMSO, the compatibility of tofacitinib citrate in DMSO might be a concern. It was observed that DMSO induced degradation of tofacitinib citrate, resulting in total degradation products of 4.17%. Surprisingly, the compatibility issue was resolved by adding propylene glycol, ethanol or isopropyl alcohol (IPA). It was found that in the presence of propylene glycol, ethanol or isopropyl alcohol, the total degradation products of tofacitinib citrate in DMSO were significantly suppressed. Therefore, a combination of DMSO with other solvents/excipients like PG, ethanol or IPA can be used in the formulation to dissolve tofacitinib citrate and at the same time reduce the total degradation products of tofacitinib citrate in DMSO.

Example 3

Preparation of Tofacitinib Topical Formulations

Based on the compatibility study result, a preliminary formulation of tofacitinib citrate was designed as follows (Table 3). DMSO, or a combination of DMSO with PG, ethanol, and/or water, was utilized as a solvent to dissolve the active ingredient tofacitinib citrate. All tofacitinib citrate should be fully dissolved as a clear solution. The formulation can utilize one or more pharmaceutically acceptable excipients to modify its characteristics or change its dosage form. Herein, sodium hydroxide was utilized as a pH adjusting agent. The quantity sufficient (q.s.) of 0.5N sodium hydroxide solution was properly added to reach the desired pH. Butylated hydroxyanisole was utilized as an antioxidant to inhibit the oxidation of the formulation. Hydroxypropyl cellulose was utilized as a thickening agent to control the rheological properties to formulate a solution or gel form. Oil phase and water phase are key components of semi-solid dosage forms. They are divided into two types: oil-in-water (O/W) form which is composed of small droplets of oil dispersed in a continuous water phase, and water-in-oil (W/O) form which is composed of small droplets of water dispersed in a continuous oily phase. Emulsifiers are compounds that typically have a polar or hydrophilic (i.e. water-soluble) part and a non-polar (i.e. hydrophobic or lipophilic) part. An emulsifier is a substance that stabilizes an emulsion by increasing its kinetic stability.

TABLE 3

Ingredients of Tofacitinib Topical Formulations

| Ingredient | Function |
|---|---|
| Tofacitinib citrate | Active ingredient |
| DMSO | Solvent |
| Propylene Glycol | Solvent |
| Ethanol | Solvent |
| 0.5N NaOH | pH adjusting agent |
| Hydroxypropyl Cellulose | Thickening agent |
| Butylated Hydroxyanisole | Antioxidant |
| Castor Oil | Oily material (oil phase) |
| Water | Water phase/Solvent |
| Hydroxyethyl acrylate/sodium acryloyldimethyl taurate copolymer | Emulsifier |

Table 4 shows twenty DMSO based tofacitinib topical formulations (P1 to P20) and an ointment formulation (C1) as a comparative example. C1 ointment is disclosed in US 20120258976, which contains free base of tofacitinib.

TABLE 4

Tofacitinib Topical Formulations

| Tofacitinib Topical Formulations | (% W/W) | | | | | | | |
|---|---|---|---|---|---|---|---|---|
| | P1 | P2 | P3 | P4 | P5 | P6 | P7 | P8 |
| Tofacitinib Free Base/Citrate salt | Citrate salt | | | | | | | |
| | 3.2 | 3.2 | 3.2 | 3.2 | 3.2 | 3.2 | 1.0 | 3.2 |
| DMSO | 45.5 | 45.5 | 45.5 | 45.5 | 45.5 | 45.5 | 45.5 | 45.5 |
| Propylene Glycol | 11 | 11 | 40 | 37.5 | 37.5 | 37.5 | 13.2 | 37.4 |
| Hydroxypropyl Cellulose | 2.5 | 2.5 | — | 2.5 | 2.5 | 4 | 2.5 | 2.5 |
| Carbomer type C | — | — | — | — | — | — | — | — |
| Purified water | 11.3 | — | 11.3 | 11.3 | — | 9.8 | 11.3 | — |
| Ethyl Alcohol 95% | 26.5 | 26.5 | — | — | — | — | 26.5 | — |
| 0.5 N NaOH | — | 11.3 | — | — | 11.3 | — | — | 11.3 |
| Butylated Hydroxyanisole | — | — | — | — | — | — | — | 0.1 |
| Oleyl Alcohol | — | — | — | — | — | — | — | — |
| Glycerin | — | — | — | — | — | — | — | — |

TABLE 4-continued

Tofacitinib Topical Formulations

| | | | | | | | | |
|---|---|---|---|---|---|---|---|---|
| PEG 400 | — | — | — | — | — | — | — | — |
| PEG 3350 | — | — | — | — | — | — | — | — |
| Total | 100 | 100 | 100 | 100 | 100 | 100 | 100 | 100 |

| Tofacitinib Topical Formulations | (% W/W) | | | |
|---|---|---|---|---|
| | P9 | P10 | P11 | C1 |
| Tofacitinib Free Base/Citrate salt | 2.0 | Free base 2.0 | 2.0 | 2.0 |
| DMSO | 45.5 | 45.5 | 45.5 | — |
| Propylene Glycol | 37.5 | 38.6 | 38.9 | 18.0 |
| Hydroxypropyl Cellulose | 2.5 | 4 | — | — |
| Carbomer type C | — | — | 1.0 | — |
| Purified water | 12.5 | 9.9 | qs | — |
| Ethyl Alcohol 95% | — | — | — | — |
| 0.5 N NaOH | — | — | adjust to pH 5-6 | — |
| Butylated Hydroxyanisole | — | 0.1 | 0.1 | 0.1 |
| Oleyl Alcohol | — | — | — | 2.0 |
| Glycerin | — | — | — | 17.9 |
| PEG 400 | — | — | — | 30.0 |
| PEG 3350 | — | — | — | 30.0 |
| Total | 100 | 100 | 100 | 100 |

| Tofacitinib Topical Formulations | (% W/W) | | | | |
|---|---|---|---|---|---|
| | P12 | P13 | P14 | P15 | P16 |
| Tofacitinib Free Base/Citrate salt | 2.0 | Free base 2.0 | 2.0 | Citrate salt 3.2 | Free base 2.0 |
| DMSO | 45.5 | 45.5 | 45.5 | 45.5 | 10 |
| Propylene Glycol | — | 5 | — | 39 | 50 |
| Hydroxypropyl Cellulose | — | — | — | — | 2.5 |
| Carbomer type C | — | — | — | 1 | — |
| Purified water | 22.4 | 6.4 | 22.4 | — | 35.4 |
| Ethyl Alcohol 95% | — | — | — | — | — |
| 0.5 N NaOH | — | — | — | 11.3 | — |
| Butylated Hydroxyanisole | 0.1 | 0.1 | 0.1 | — | 0.1 |
| Butylated Hydroxytoluene | | | | | |
| Tween 60 | 5 | — | 5 | — | — |
| Span 60 | 5 | — | 5 | — | — |
| Mineral Oil | 10 | — | 20 | — | — |
| Caster Oil | | | | | |
| White Petrolatum | 5 | 40 | — | — | — |
| Glyceryl monostearate | 5 | — | — | — | — |
| Sodium lauryl sulfate | — | 1 | — | — | — |
| Edetate Disodium, 2H$_2$O | | | | | |
| Methylparaben | | | | | |
| hydroxyethyl acrylate/sodium acryloyldimethyl taurate copolymer | | | | | |
| Total | 100 | 100 | 100 | 100 | 100 |

| Tofacitinib Topical Formulations | (% W/W) | | | |
|---|---|---|---|---|
| | P17 | P18 | P19 | P20 |
| Tofacitinib Free Base/Citrate salt | 3.2 | Citrate Salt 3.2 | 3.2 | 3.2 |
| DMSO | 42.5 | 42.5 | 42.5 | 20 |
| Propylene Glycol | 40.1 | 39.82 | 39.87 | 10 |
| Hydroxypropyl Cellulose | 2.5 | 2.5 | 2.5 | — |
| Carbonier type C | — | — | — | — |
| Purified water | — | — | — | 51.6 |
| Ethyl Alcohol 95% | — | — | — | — |
| 0.5 N NaOH | 11.0 | 11.3 | 11.3 | — |
| Butylated Hydroxyanisole | 0.45 | 0.45 | 0.45 | 1.0 |
| Butylated Hydroxytoluene | 0.18 | 0.18 | 0.18 | 0.2 |
| Tween 60 | — | — | — | — |
| Span 60 | — | — | — | — |
| Mineral Oil | — | — | — | — |
| Caster Oil | — | — | — | 10 |
| White Petrolatum | — | — | — | — |
| Glyceryl monostearate | — | — | — | — |
| Sodium lauryl sulfate | — | — | — | — |

TABLE 4-continued

| Tofacitinib Topical Formulations | | | | |
|---|---|---|---|---|
| Edetate Disodium, 2H$_2$O | 0.01 | — | — | — |
| Methylparaben | 0.05 | 0.05 | — | — |
| hydroxyethyl acrylate/sodium acryloyldimethyl taurate copolymer | | | | 4 |
| Total | 100 | 100 | 100 | 100 |

The DMSO based formulations were prepared by the following steps:

1. Prepare API/DMSO Solution: dissolve the active agent (tofacitinib free base or citrate salt) in DMSO;
2. Prepare Thickening/Gelling Solution: dissolve a thickening agent or gelling agent in a solvent (e.g., propylene glycol and/or ethanol) if necessary,
3. Prepare Chelating Solution: dissolve a chelating agent in a sodium hydroxide solution if necessary;
4. Prepare API/DMSO Mixing Solution: add an antioxidant, the chelating solution, a preservative, an oily material, an emulsifier, or other pharmaceutically acceptable excipients into the API/DMSO solution if necessary;
5. Add the API/DMSO Mixing solution into water if necessary; and
6. Add the API/DMSO Mixing solution into the Thickening/Gelling Solution if necessary; and
7. Keep stirring until all the compositions were homogenous.

Example 4

Stability Study of Tofacitinib Topical Formulations

The nine formulations (P1 to P6, P8, P9 and C1) were subjected to the stability study at 25° C./60% relative humidity (RH) and 40° C./75% relative humidity for at least 1 month. The one month stability result of the nine formulations was summarized in Table 5. The physical and chemical stability was also evaluated. Stability data of the formulation (P8) for an extended period were collected in Table 6.

TABLE 5

Stability of Nine Formulations

| Formulation | P1 | P2 | P3 | P4 | P5 |
|---|---|---|---|---|---|
| Tofacitinib form | citrate | | | | |
| Initial pH | 5.16 | 6.28 | 4.70 | 4.76 | 5.88 |
| Total degradation products (% w/w) | | | | | |
| Initial | 0.03 | 0.03 | 0.04 | 0.06 | 0.13 |
| 25° C./60% RH, 1 Month | 0.06 | 0.07 | 0.12 | 0.21 | 0.12 |
| 40° C./75% RH, 1 Month | 0.29 | 0.80 | 1.17 | 1.29 | 0.17 |
| Increased after 40° C./75% RH, 1 Month | 0.26 | 0.77 | 1.13 | 1.23 | 0.04 |
| Physical property | crystalline precipitate | crystalline precipitate | freely runny | Non-runny Preferred candidate | Non-runny Preferred candidate |

TABLE 5-continued

| Formulation | P6 | P8 | P9 | C1 |
|---|---|---|---|---|
| Tofacitinib form | citrate | | Free base | |
| Initial pH | 4.77 | N/A | 6.05 | N/A |
| Total degradation products (% w/w) | | | | |
| Initial | 0.04 | 0.08 | 0.82 | 2.65 |
| 25° C./60% RH, 1 Month | 0.19 | 0.08 | 1.19 | 4.03 |
| 40° C./75% RH, 1 Month | 1.01 | 0.35 | 1.25 | 6.14 |
| Increased after 40° C./75% RH, 1 Month | 0.97 | 0.27 | 0.43 | 3.49 |
| Physical property | crystalline precipitate | Non-runny Preferred candidate | Non-runny Preferred candidate | poor stability |

TABLE 6

| Stability Data of the Formulation P8 for an Extended Period | | Total degradation products (% w/w) |
|---|---|---|
| 25° C./60% RH | Initial | 0.08 |
| | 3 Months | 0.08 |
| | 4 Months | 0.08 |
| | 5 Months | 0.09 |
| | 6 Months | 0.48 |
| | 8 Months | 0.77 |
| 40° C./75% RH | Initial | 0.08 |
| | 1 Month | 0.35 |

C1 ointment formulation shows poor stability, and the weight percentage of total degradation products is 6.14%. The other formulations, P1-P6, P8 and P9, show better stability when compared to C1 ointment formulation. In sum, the DMSO based formulations (P1 to P6, P8 and P9) exhibit higher stability than the ointment formulation (C1), whether tofacitinib is in the form of free base or citrate salt. Moreover, the stability result of the formulation P8 reveals great stability at more than 1 month. The weight percentage of total degradation products is merely 0.77% at 25° C./60% relative humidity (RH) for 8 months.

However, crystalline precipitate was observed in P1, P2 and P6. P3 is less preferred due to its freely runny property. It is inconvenient to apply on a lesion site when formulations tend to flow freely. Therefore, P4, P5, P8 and P9 are preferred formulation candidates.

Example 5

In-Vitro Penetration/Retention Study of Tofacitinib Topical Formulations

A number of formulations containing tofacitinib free base or citrate salt were subjected to in-vitro penetration/retention study. Generally, both hairless guinea pig and pig are wellestablished models for predicting human skin absorption. By contrast, other models using laboratory animals such as rat, rabbit, and guinea pig with hair often result in overrating the human skin absorption. Flank skin obtained from seven months-old pig (Landrace pig and Duroc pig crossbreed) in Taiwan Livestock Company was used as a penetration membrane. Vertical diffusion cell (USP/NF<725>, FIG. 1) was applied for the penetration/retention test. Specifically, hair on the skin was clipped before dermatoming to a thickness of 750 Electrical resistance of the skin was confirmed to ensure the skin integrity. The skin was placed on the top of diffusion cell in contact with receptor phase, which was filled with phosphate buffered saline (PBS) (pH 7.4) with 20% polyethylene glycol 300 (PEG 300) (at 37° C.). Approximately 280 mg of tofacitinib formulations were added onto the skin surface in the donor compartment. After 8 hours, the residual formulation on the skin surface was removed and skin surface was again cleaned carefully. Stratum corneum was removed and the skin was weighed and minced, and extracted with acetonitrile/methanol/water extraction solution by vigorous shaking for 1 hour. The skin extracts were centrifuged and analyzed by high performance liquid chromatography (HPLC).

The relative tofacitinib amounts of skin extract (µg)/receiver (µg) are shown in TABLE 7. The data shows that P1 to P6 and P9 are all higher than C1. It indicates that P1 to P6 and P9 DMSO based formulations tend to keep tofacitinib in the skin more than to penetrate across the skin.

TABLE 7

The Relative Amount of Skin Extract/Receiver of P1 to P6, P9 and C1

| Formulation | Skin extract/Receiver (range) |
|---|---|
| P1 | 13.8 (9.8-17.4) |
| P2 | 32.7 (24.8-40.8) |
| P3 | 101.0 (11.9-246.4) |
| P4 | 125.6 (77.9-235.2) |
| P5 | 128.2 (72.3-242.5) |
| P6 | 138.7 (70.8-199.5) |
| P9 | 31.2 (9.8-59.6) |
| C1 | 4.7 (2.5-6.4) |

Figure 2:
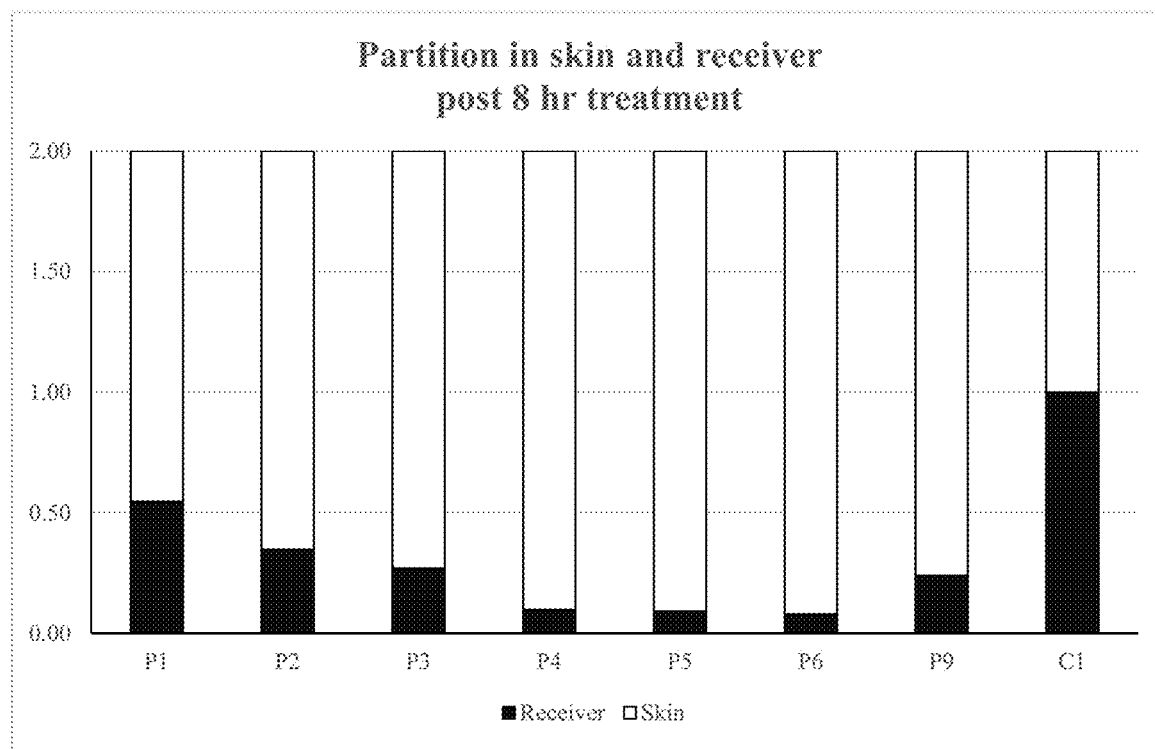
FIG. 2 is a statistical bar graph showing normalized partition results of tofacitinib in skin and receiver.

FIG. 2 shows the partition in skin and the receiver after 8 hours treatment. Comparing the DMSO based formulations (P1 to P6 and P9) with C1, the results showed that tofacitinib ointment (C1) had the highest partition in the receiver and the lowest in skin, indicating that this formulation facilitates tofacitinib penetrating across skin into the blood or systemic circulation more than that retaining in skin among all the formulations. This result suggests that the DMSO based formulations not only improve the stability of the product, but also increase the amounts of tofacitinib retained in the skin.

Formulations P1 and P2 have the highest partitions in the receiver among all the DMSO based formulations. This might be attributable to ethyl alcohol in the formulation that enhances the penetration of tofacitinib into the receiver and reduces the portion in skin accordingly. Therefore, DMSO based formulations without ethyl alcohol are more preferred than those added with ethyl alcohol.

Comparing P4 (without 0.5N NaOH) and P5 (with 0.5N NaOH), adding sodium hydroxide to change the pH of the formulation did not make significant difference for the penetration/retention of tofacitinib. In sum, the formulations P4, P5 and P6 exhibit highest amounts of tofacitinib retained in the skin than that penetrating through the skin into the blood or systemic circulation.

Example 6

More Excipient Effects on the Partition of Tofacitinib in Epidermis, Dermis, and the Receiver An individual study was performed to see the effect of the antioxidant agent, butylated hydroxyanisole (BHA), on the partition of tofacitinib in epidermis, dermis, and the receiver. Four months-old pig (Landrace pig and Duroc pig crossbreed) flank skin obtained from PigModel Animal Technology Co., Ltd. was used in in-vitro penetration/retention study. Formulation P8 is a modified formulation by adding 0.1% BHA in comparison to P5 formulation (Table 4). Approximately 280 mg of P5 or P8 were added onto the skin surface in the donor compartment. After 8 hours, the residual formulation on the skin surface was removed and cleaned carefully. Stratum corneum was removed and the skin was then heat-separated into epidermis and dermis. The separated epidermis and dermis were weighed and extracted. Together with receiver samples, both epidermis and dermis extracts were submitted to HPLC analyses for the concentrations of tofacitinib citrate. Results are shown in below Table 8.

The results showed that BHA didn't make significant difference in the skin extracts and receivers, indicating that the antioxidant BHA was not critical to the partition of tofacitinib in the skin.

TABLE 8

Levels of Tofacitinib Citrate in Epidermis, Dermis and Receivers after 8-hr Application of Topical Formulations P5 and P8

| Formulation | Epidermis (µg/g) | Dermis (µg/g) | Receiver (ng/cm$^2$) |
|---|---|---|---|
| P5 | 176.45 ± 122.93 | 7.58 ± 4.70 | 66.29 ± 40.12 |
| P8 | 292.93 ± 104.41 | 13.22 ± 8.67 | 21.06 ± 17.23 |

Example 7

The Ratio of Solvent/Tofacitinib Effect on the Partition of Tofacitinib in Epidermis, Dermis, and the Receiver with Time Course An in-vitro penetration/retention study was conducted to compare the cumulative amounts of tofacitinib retained in the skin and entering into receivers with time course. This experiment aims to investigate the effect of the ratio of solvent/tofacitinib on the penetration/retention, so as to ensure that DMSO based formulations have a preference of tofacitinib retention in skin across all the time course up to 12 hours.

Formulations P5 and P7 were shown in Table 4, P7 has a higher DMSO/tofacitinib ratio comparing with P5's. Approximately 280 mg of tofacitinib formulations were added onto the skin surface (1 cm$^2$) in the donor compartment. The dermal side of each skin section was in contact with receiver medium. A uniform, 37° C. temperature was achieved within the receiver chamber by circulating water through the cell jacket. After 4, 8, and 12 hours from the administration, receiver solutions were collected and epidermis and dermis were separated and extracted. Tofacitinib concentrations in skin extracts and receiver solutions were analyzed by HPLC.

Figure 3:
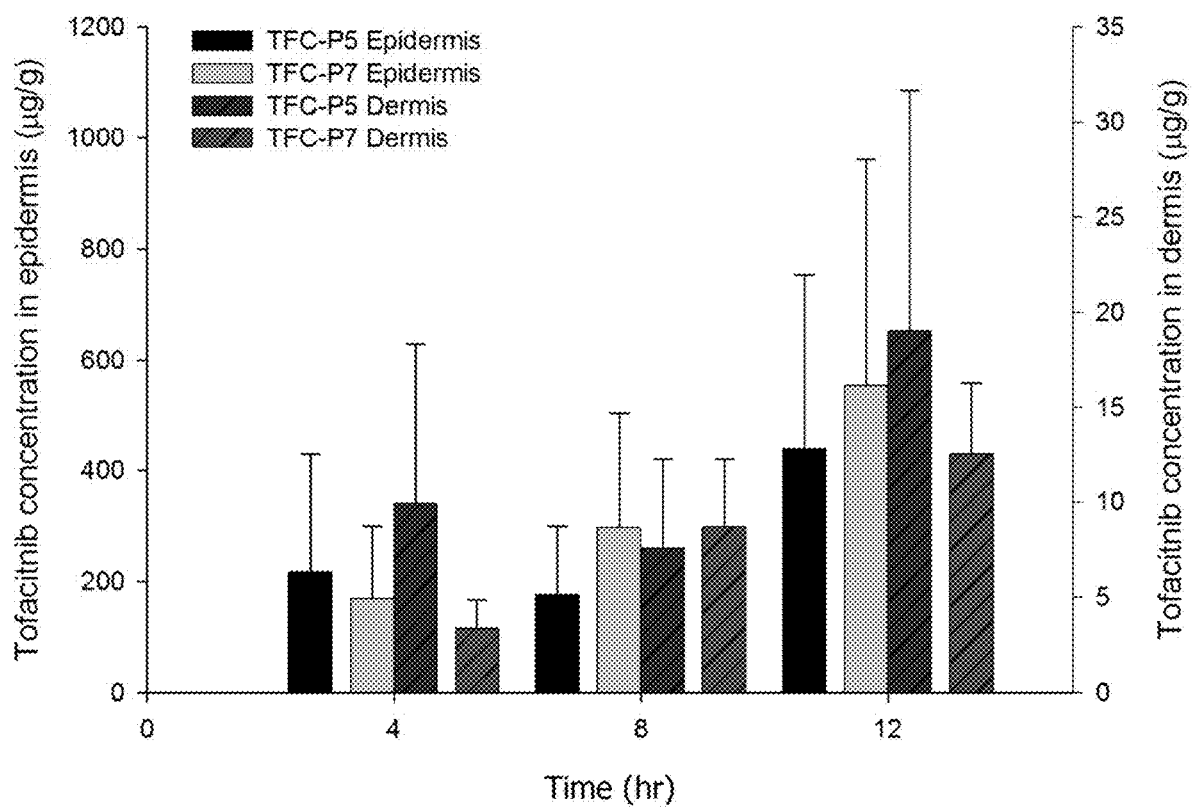
FIG. 3 is a statistical bar graph showing tofacitinib concentrations in epidermis and dermis with time course.
Figure 4:
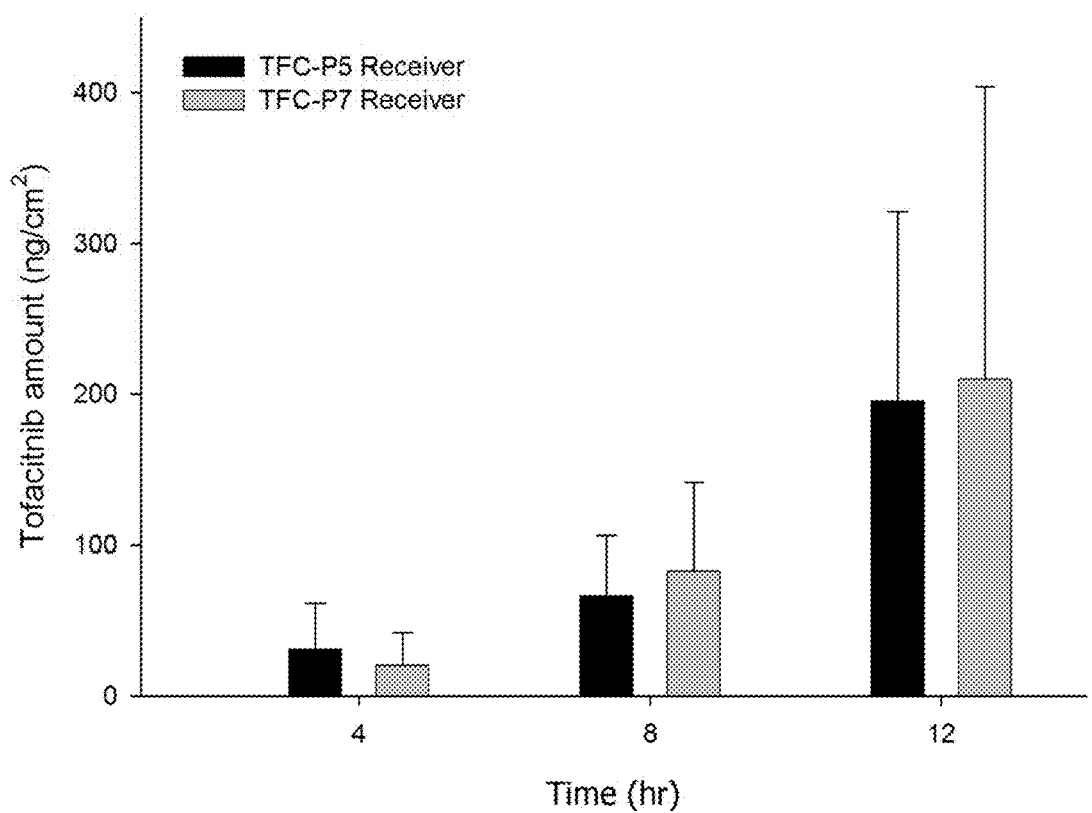
FIG. 4 is a statistical bar graph showing tofacitinib concentrations in the receiver with time course.

As shown in FIGS. 3 and 4, P5 and P7 had comparable tofacitinib levels in epidermis and dermis as well as in the receiver solutions at the three time points, indicating that a higher DMSO/API ratio could achieve similar penetration/retention effect.

According to the above studies, the topical tofacitinib formulation of the present invention tends to be retained in the skin and has relatively low concentrations in the receivers during the period up to 12 hours after administration. Therefore, the formulation of the present invention may have lower systemic exposure of tofacitinib and thus can reduce the systemic side effects as compared with oral dosage forms and C1 ointment.

Example 8

Clinical Trials of Tofacitinib Topical Formulations in the Treatment of Atopic Dermatitis A randomized, double-blinded, placebo-controlled study was designed and 6 evaluable patients received either placebo or the tofacitinib topical formulations of the present invention at ratio of 1:2. The purpose of this study is to evaluate the efficacy of the tofacitinib topical formulations of the present invention twice daily (BID) in patients with atopic dermatitis compared to placebo (vehicle). Either tofacitinib topical formulations or placebo were applied over the targeted skin corresponding to 16 to 100 cm² area twice daily (BID) for 8 consecutive weeks.

The Atopic Dermatitis Severity Index (ADSI) was used to assess the severity of the dermatitis. This index (range, 0-15) consists of the sum of the scores for pruritus, erythema, exudation, excoriation, and lichenification, all scored on a 4-point (range, 0-3) scale. At Week 0 (baseline), 2, 4, and 8, ADSI were scored. Efficacy endpoints included total clearance (ADSI=0), partial clearance (0<ADSI≤2) and ≥4-point improvement from Week 0 (baseline) (Baseline minus Visit score) in ADSI at Week 2, 4, and 8.

Table 8 shows the clinical study result of ADSI at Week 0, 2, 4 and 8. Compare Week 2 and Week 0 (baseline), the sum score of ADSI in all subjects receiving the tofacitinib topical formulations of the present invention significantly decrease. And they achieved the efficacy endpoint that ADSI is clearance (ADSI=0) or partial clearance (0<ADSI≤2) at Week 8. The Average ADSI score and ADSI score improvement were calculated in Table 9. The Average ADSI score improvement of the subjects receiving tofacitinib topical formulations of the present invention dramatically increase to 3.75 at Week 2. Then it slightly increases to 4.75 at Week 4 and eventually to 5 at Week 8. Compare to the subjects with tofacitinib, the subjects with placebo exhibits only 1.5 at Week 2, then down to 1 at Week 4 and eventually increase to 3.5 at week 8.

According to the above studies, the conditions of atopic dermatitis of the subjects receiving the tofacitinib topical formulations of the present invention were dramatically improved in 2 weeks and the efficacy was achieved in 8 weeks. Therefore, the subjects who received the tofacitinib topical formulations of the present invention exhibited much better improvement for at least 8 weeks than the subjects receiving placebo.

TABLE 8

Clinical study result of ADSI at Week 2, 4 and 8

| received | subjects | ADSI score | Week 0 | Week 2 | Week 4 | Week 8 |
|---|---|---|---|---|---|---|
| Placebo | R1 | Erythema | 2 | 2 | 2 | 2 |
| | | Pruritus | 2 | 2 | 3 | 1 |
| | | Exudtion | 1 | 1 | 1 | 0 |
| | | Excoriation | 1 | 1 | 1 | 0 |
| | | Lichenification | 1 | 1 | 2 | 1 |
| | | SUM | 7 | 7 | 9 | 4 |
| | R2 | Erythema | 1 | 1 | 0 | 0 |
| | | Pruritus | 2 | 0 | 0 | 0 |
| | | Exudtion | 0 | 0 | 0 | 0 |
| | | Excoriation | 1 | 0 | 0 | 0 |
| | | Lichenification | 1 | 1 | 1 | 1 |
| | | SUM | 5 | 2 | 1 | 1 |
| Tofacitinib | R3 | Erythema | 2 | 1 | 1 | 1 |
| | | Pruritus | 1 | 0 | 0 | 0 |
| | | Exudtion | 1 | 0 | 0 | 0 |
| | | Excoriation | 2 | 1 | 0 | 1 |
| | | Lichenification | 1 | 0 | 0 | 0 |
| | | SUM | 7 | 2 | 1 | 2 |
| | R4 | Erythema | 2 | 1 | 0 | 1 |
| | | Pruritus | 2 | 1 | 0 | 0 |
| | | Exudtion | 0 | 0 | 0 | 0 |
| | | Excoriation | 1 | 1 | 0 | 1 |
| | | Lichenification | 2 | 0 | 1 | 0 |
| | | SUM | 7 | 3 | 1 | 2 |
| | R5 | Erythema | 2 | 1 | 0 | 0 |
| | | Pruritus | 1 | 1 | 1 | 1 |
| | | Exudtion | 1 | 0 | 1 | 0 |
| | | Excoriation | 2 | 1 | 1 | 0 |
| | | Lichenification | 2 | 2 | 2 | 1 |
| | | SUM | 8 | 5 | 5 | 2 |
| | R6 | Erythema | 2 | 0 | 0 | 0 |
| | | Pruritus | 1 | 1 | 0 | 0 |
| | | Exudtion | 1 | 0 | 0 | 0 |
| | | Excoriation | 0 | 0 | 0 | 0 |
| | | Lichenification | 0 | 0 | 0 | 0 |
| | | SUM | 4 | 1 | 0 | 0 |

TABLE 9

Average ADSI score and ADSI score Improvement at Week 2, 4 and 8
Average ADSI score range, 0-15)

| | Week 0 | Week 2 | Week 4 | Week 8 |
|---|---|---|---|---|
| Placebo (n = 2) | 6 | 4.5 | 5 | 2.5 |
| Tofacitinib (n = 4) | 6.5 | 2.75 | 1.75 | 1.5 |
| Average ADSI score Improvement | | | | |
| Placebo (n = 2) | 0 | 1.5 | 1 | 3.5 |
| Tofacitinib (n = 4) | 0 | 3.75 | 4.75 | 5 |

Example 9

Clinical Trials of Tofacitinib Topical Formulations in the Treatment of Vitiligo A randomized, double-blind, placebo-controlled, within-subject controlled, proof-of-concept study was carried out to characterize the efficacy of the tofacitinib topical formulations of the present invention topically administered BID (twice daily) for up to 12 weeks in subjects with vitiligo.

A total of 10 subjects were enrolled and randomized. Each target depigmentation areas localized to the face/neck/arms/legs/trunk of eligible subjects received either the tofacitinib topical formulation or placebo. Treatments were applied topically BID for up to 12 weeks at an application coverage of approximately 3 mg/cm². All patients were evaluated at baseline and monthly intervals for clinical improvement (repigmentation level) and photographs.

Figure 5:
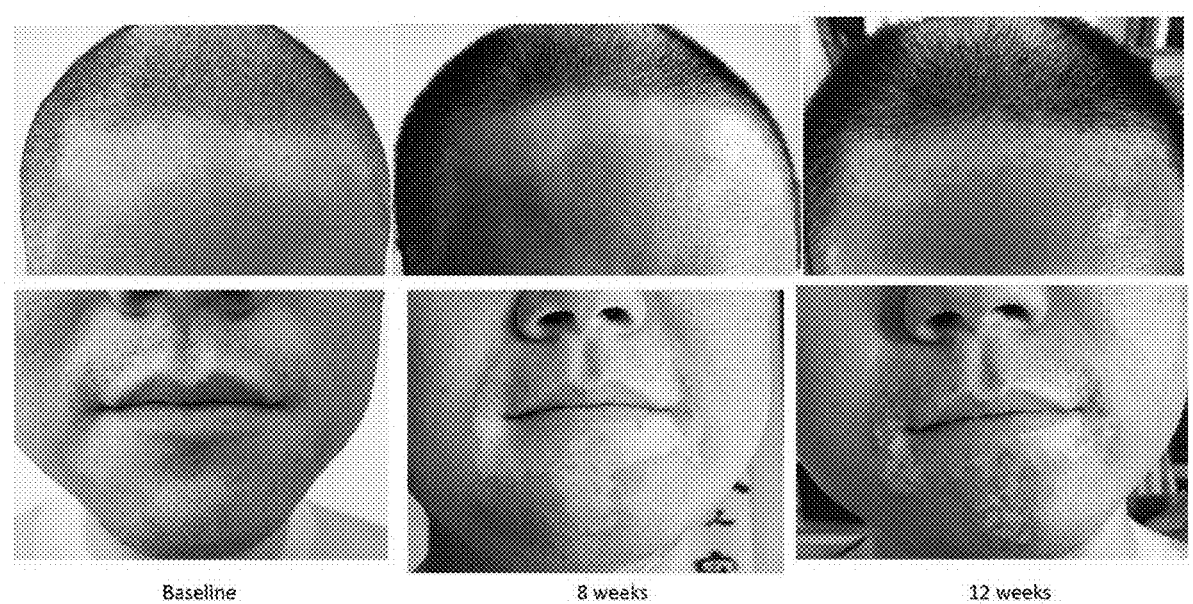
FIG. 5 shows photographs of a male subject with facial vitiligo from baseline, 8 weeks and 12 weeks of treatment with the tofacitinib topical formulation of the present invention.

FIG. 5 shows photographs of a male subject with facial vitiligo from baseline, 8 weeks and 12 weeks of treatment with the tofacitinib topical formulation of the present invention. A significant repigmentation of the forehead (percent improvement≅30%) and chin (percent improvement 60%) was observed from baseline through 12 weeks.

Figure 6:
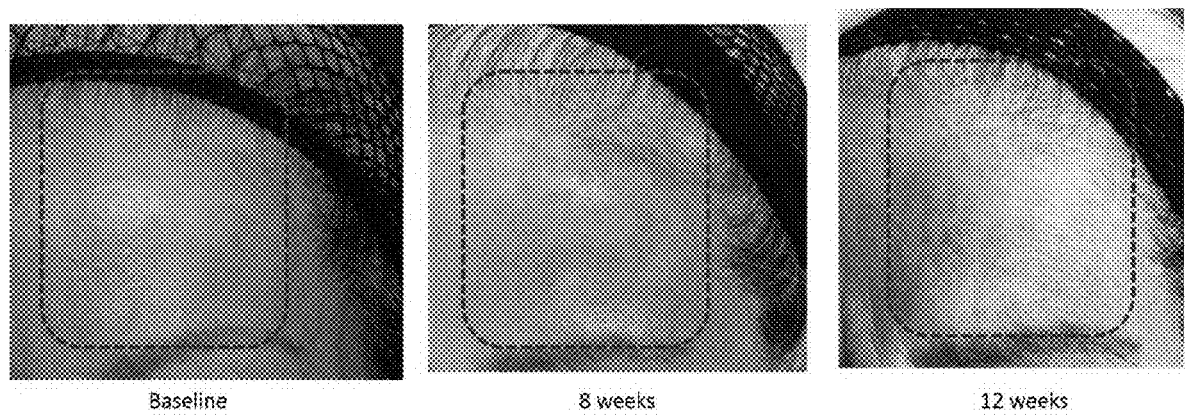
FIG. 6 shows photographs of a female subject with facial vitiligo from baseline, 8 weeks and 12 weeks of treatment with the tofacitinib topical formulation of the present invention.

FIG. 6 shows photographs of a female subject with facial vitiligo from baseline, 8 weeks and 12 weeks of treatment with the tofacitinib topical formulation of the present invention. A significant repigmentation of the forehead (percent improvement≅90%) was nearly completed from baseline through 12 weeks.

The above disclosure is related to the detailed technical contents and inventive features thereof. People skilled in this field may proceed with a variety of modifications and replacements based on the disclosures and suggestions of the invention as described without departing from the characteristics thereof.

What is claimed is:

1. A method for treating an autoimmune disease in a subject, comprising administering a topical formulation to said subject, wherein the topical formulation comprises:
    (a) a therapeutically effective amount of tofacitinib;
    (b) at least one solvent comprising dimethyl sulfoxide (DMSO) and propylene glycol; and
    (c) optionally, one or more other pharmaceutically acceptable excipients.

2. The method of claim 1, wherein said autoimmune disease is selected from vitiligo, atopic dermatitis, psoriasis, epidermolysis bullosa acquista, pemphigus vulgaris, IgA-mediated bullous dermatoses, systemic lupus erythematosus, alopecia areata, porphyria, scleroderma, rheumatoid arthritis, multiple sclerosis and skin complication of Type I diabetes.

3. The method of claim 1, wherein tofacitinib is administered to the skin at a daily therapeutically effective dose of about 0.5 mg/cm² to about 60 mg/cm².

4. The method of claim 1, wherein the topical formulation is in the form selected from the group consisting of a solution, a suspension, a cream, an ointment, a lotion and a gel.

5. The method of claim 1, wherein the topical formulation is in the form selected from a solution and a gel.

6. The method of claim 1, wherein said tofacitinib is in the form of a pharmaceutically acceptable salt selected from citrate salt, hydrochloride salt, hydrobromide salt, oxalate salt, nitrate salt, sulfate salt, phosphate salt, fumarate salt, succinate salt, maleate salt, besylate salt, tosylate salt, palmitate salt and tartrate salt.

7. The method of claim 6, wherein said pharmaceutically acceptable salt is citrate salt.

8. The method of claim 1, wherein said solvent further comprises at least one of propylene glycol, ethanol, and water.

9. The method of claim 1, wherein said pharmaceutically acceptable excipient is selected from the group consisting of a thickening agent, a stabilizer, an antioxidant, a chelating agent, an oily material, an emulsifier, a penetration enhancer, a pH adjusting agent, a preservative, an antimicrobial agent, an opacifier, a fragrance, a colorant, a gelling agent, a moisturizer, a surfactant, and a combination thereof.

10. The method of claim 1, wherein said pharmaceutically acceptable excipient is a thickening agent.

11. The method of claim 10, wherein said thickening agent is selected from the group consisting of a cellulose derivative, polyvinylpyrrolidone, a carbomer polymer, carbomer derivative, maltodextrin, polydextrose, dextrates, carboxypolymethylene, polyvinyl alcohol, poloxamers, polyethylene glycols and mixtures thereof.

12. The method of claim 1, wherein when the formulation is applied to the skin of a subject, the amount of tofacitinib retained in the skin is more than that penetrating through the skin into the blood or systemic circulation, for 4 hours after the application.

13. The method of claim 1, wherein when the formulation is applied to the skin of a subject, the amount of tofacitinib retained in the skin is at least about 4.7 times more than that penetrating through the skin into the blood or systemic circulation, for 8 hours after the application.

14. The method of claim 1, wherein less than 2% of total degradation products are observed after stored at room temperature for at least 1 month.

15. A method for treating an autoimmune disease in a subject, comprising administering the topical formulation to said subject, wherein the topical formulation comprises:
    (a) a therapeutically effective amount of tofacitinib citrate;
    (b) dimethyl sulfoxide;
    (c) propylene glycol;
    (d) optionally, a thickening agent;
    (e) optionally, an antioxidant; and
    (f) optionally, one or more other pharmaceutically acceptable excipients.

16. The method of claim 15, comprising:
    (a) about 0.1% w/w to about 5% w/w of tofacitinib citrate;
    (b) about 1% w/w to about 80% w/w of dimethyl sulfoxide;
    (c) about 10% w/w to about 60% w/w of propylene glycol;
    (d) optionally, about 0.05% w/w to about 5% w/w of hydroxypropyl cellulose;
    (e) optionally, about 0.05% w/w to about 5% w/w of butylated hydroxyanisole; and
    (f) optionally, one or more other pharmaceutically acceptable excipients,
    based on the total weight of the topical formulation.

* * * * *